(12) United States Patent
Suga

(10) Patent No.: US 9,417,445 B2
(45) Date of Patent: Aug. 16, 2016

(54) IMAGE-ACQUISITION DEVICE

(71) Applicant: OLYMPUS CORPORATION, Tokyo (JP)

(72) Inventor: Takeshi Suga, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/019,447

(22) Filed: Feb. 9, 2016

(65) Prior Publication Data

US 2016/0161732 A1  Jun. 9, 2016

Related U.S. Application Data

(63) Continuation of application No. PCT/JP2014/078451, filed on Oct. 27, 2014.

(30) Foreign Application Priority Data

Oct. 30, 2013  (JP) .................................. 2013-225634

(51) Int. Cl.

| G02B 26/08 | (2006.01) |
|---|---|
| G02B 23/02 | (2006.01) |
| A61B 1/00 | (2006.01) |
| A61B 1/05 | (2006.01) |
| G02B 13/04 | (2006.01) |
| G02B 13/22 | (2006.01) |
| G02B 23/24 | (2006.01) |
| G02B 5/04 | (2006.01) |

(52) U.S. Cl.
CPC ............ *G02B 23/02* (2013.01); *A61B 1/00096* (2013.01); *A61B 1/00188* (2013.01); *A61B 1/05* (2013.01); *G02B 13/04* (2013.01); *G02B 13/22* (2013.01); *G02B 23/243* (2013.01); *G02B 26/0891* (2013.01); *G02B 5/04* (2013.01)

(58) Field of Classification Search
CPC .. G02B 23/243; G02B 23/02; G02B 26/0891; G02B 15/02; G02B 13/10; G02B 13/08; G02B 13/22; G02B 13/04; G02B 5/04; A61B 1/00096; A61B 1/00188; A61B 1/05
USPC ................ 359/209.1–211.5, 226.2, 661, 740; 600/109; 348/65
See application file for complete search history.

(56) References Cited

U.S. PATENT DOCUMENTS

| 2002/0022767 A1 | 2/2002 | Dohi et al. |
| 2004/0233525 A1 | 11/2004 | Niino et al. |
| 2005/0119529 A1* | 6/2005 | Farr ..................... G02B 25/001 600/160 |

FOREIGN PATENT DOCUMENTS

| JP | 11-249014 | 9/1999 |
| JP | 2002-000550 | 1/2002 |
| JP | 2004-333712 | 11/2004 |
| JP | 2008-237916 | 10/2008 |
| JP | 2008-249838 | 10/2008 |

* cited by examiner

*Primary Examiner* — James Phan
(74) *Attorney, Agent, or Firm* — Kenyon & Kenyon LLP

(57) ABSTRACT

An image-acquisition device is consists of a single objective optical system; an image-acquisition element that acquires an image of an optical image of an object formed by the objective optical system; an optical component that can be inserted into and removed from the optical axis of the objective optical system, at an intermediate position on the optical axis; and a moving mechanism that moves the optical component between a position on the optical axis of the objective optical system and a position off the optical axis. The optical component has a deflecting surface for deflecting the optical axis of the objective optical system and a refracting surface having power.

5 Claims, 10 Drawing Sheets

IMAGE-ACQUISITION DEVICE

CROSS-REFERENCE TO RELATED APPLICATIONS

This is a continuation of International Application PCT/JP2014/078451, with an international filing date of Oct. 27, 2014, which is hereby incorporated by reference herein in its entirety. This application claims the benefit of Japanese Patent Application No. 2013-225634 filed on Oct. 30, 2013, the content of which is incorporated herein by reference.

TECHNICAL FIELD

The present invention relates to image-acquisition devices.

BACKGROUND ART

In the related art, there are known oblique viewing endoscopes for acquiring a field of view in an oblique direction, having a prism provided on the optical axis of an objective optical system (for example, see PTL 1). The prism has a wedge shape having an inclined surface inclined with respect to the optical axis of the objective optical system, and, as a result of the optical axis of the objective optical system on the incident side being deflected by the inclined surface, a field of view located in an oblique direction is observed.

By inserting and removing this wedge-shaped prism into and from the optical axis of a direct-view objective optical system, the observation direction can be switched between direct-view observation and oblique-view observation. When the prism is inserted into the optical axis of the objective optical system, the air-equivalent length on the optical axis of the objective optical system changes, displacing the focus point from the appropriate position.

CITATION LIST

Patent Literature {PTL 1} Japanese Unexamined Patent Application, Publication No. 2002-550

SUMMARY OF INVENTION

An aspect of the present invention is an image-acquisition device consisting of a single objective optical system; an image-acquisition element that captures an image of an optical image of an object formed by the objective optical system; an optical component that is inserted into and removed from an optical axis of the objective optical system, at an intermediate position on the optical axis; and a moving mechanism that moves the optical component between a first position on the optical axis of the objective optical system and a second position off the optical axis. The optical component has a deflecting surface for deflecting the optical axis of the objective optical system and a refracting surface having power.

DESCRIPTION OF EMBODIMENTS

An image-acquisition device 1 according to an embodiment of the present invention will be described below with reference to the drawings.

Figure 1:
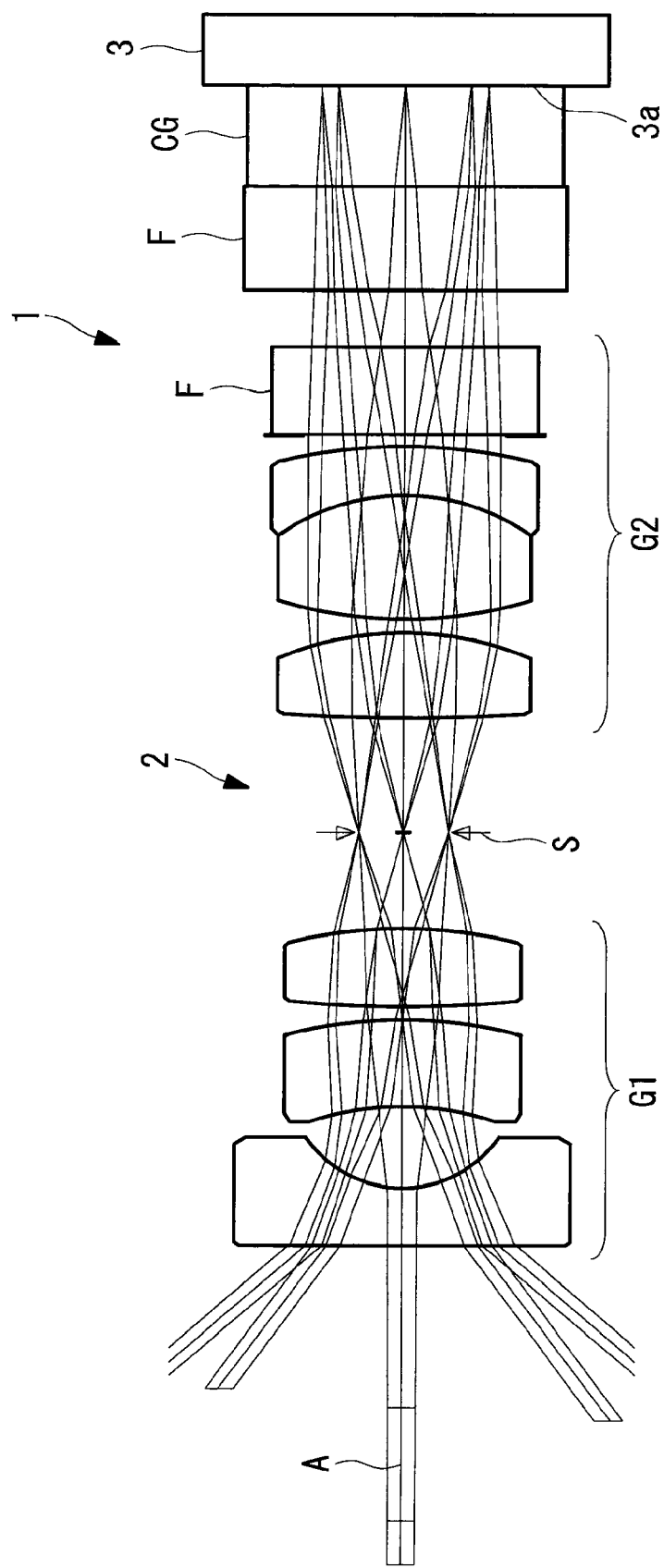
FIG. 1 shows the overall configuration of an image-acquisition device according to an embodiment of the present invention, in a direct-view observation state.
Figure 2:
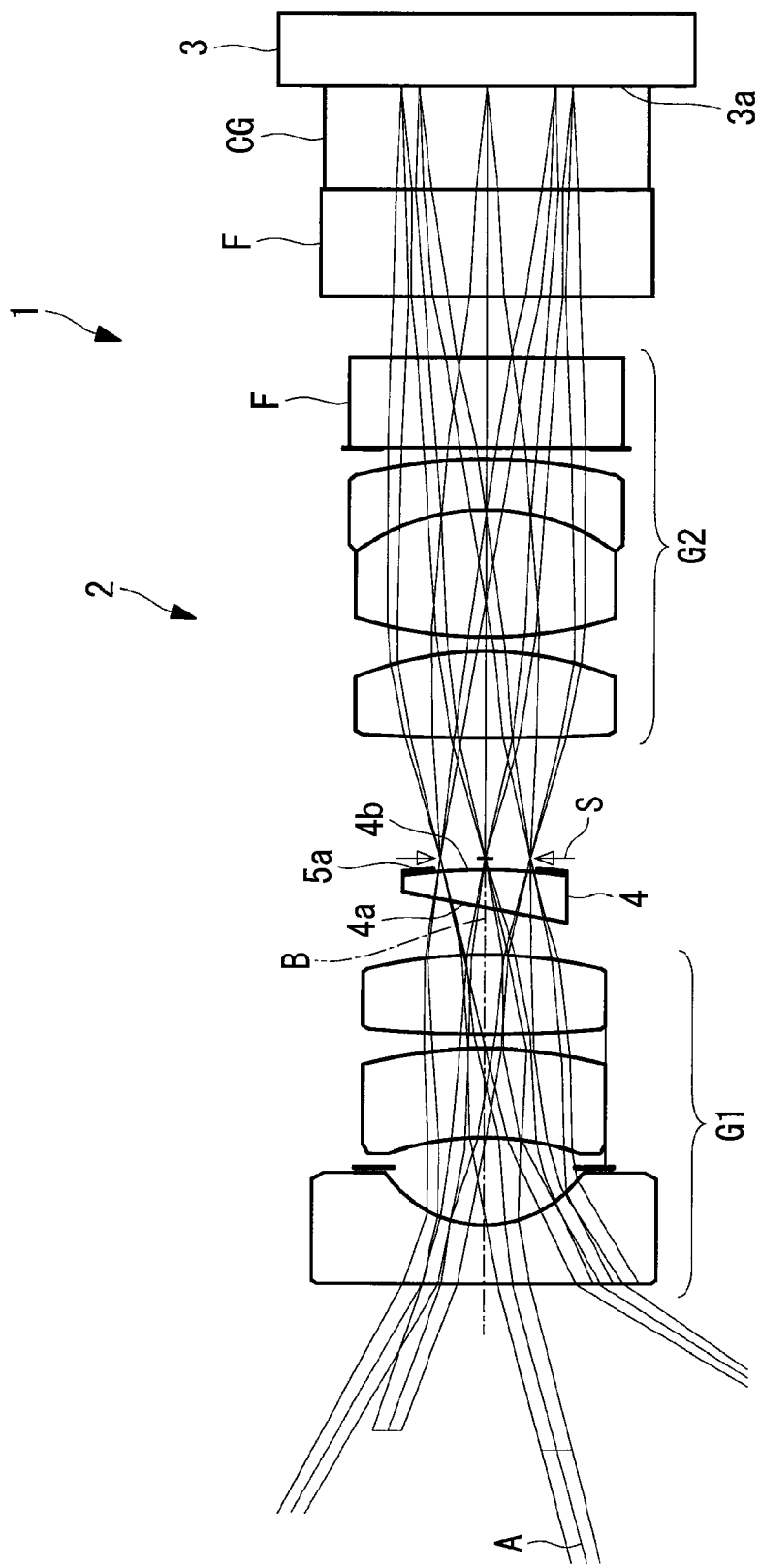
FIG. 2 is the overall configuration of the image-acquisition device according to the embodiment of the present invention, in an oblique-view observation state.

As shown in FIGS. 1 and 2, the image-acquisition device 1 according to this embodiment includes a single objective optical system 2 that forms an optical image of an object, an image-acquisition element 3 that acquires an image of the optical image formed by the objective optical system 2, a wedge-shaped prism (optical component) 4, and a moving mechanism 5 that inserts and removes the prism 4 into and from an optical axis A of the objective optical system 2. Note that, in FIGS. 1, 2, and 9, to avoid the figures becoming complicated, in the configuration of the moving mechanism 5, only a frame 5a (described below) is shown.

FIG. 1 shows a direct-view observation state, in which a position directly in front of the objective optical system 2 is observed, without the prism 4 being disposed on the optical axis A. FIG. 2 shows an oblique-view observation state, in which a position obliquely forward of the objective optical system 2 is observed, with the prism 4 being disposed on the optical axis A. As illustrated, in the direct-view observation state, the objective optical system 2 has a straight optical axis A, which extends along the central axis thereof, and, in the oblique-view observation state, the objective optical system 2 has an optical axis A, which is inclined with respect to the central axis, on the incident side of the prism 4, due to the deflecting effect of the prism 4. Thus, as will be described in detail below, the image-acquisition device 1 according to this embodiment can switch the observation direction between the direct view and the oblique view simply with the movement of the prism 4, and it is suitably applied to an endoscope in which it is difficult to change the orientation of the objective optical system 2.

In this example, the objective optical system 2 includes a first group G1, an aperture stop S, and a second group G2, in this order from the object side. The first group G1 and the second group G2 each include at least one lens. Reference sign F denotes a parallel plate, such as a filter, and reference sign CG denotes a cover glass that covers an image-acquisition surface 3a of the image-acquisition element 3. The objective optical system 2 is optimized so as to be able to obtain a good optical performance in the direct-view observation state in FIG. 1.

The prism 4 includes a deflecting surface 4a and a refracting surface 4b facing each other. The deflecting surface 4a is a flat surface inclined with respect to a predetermined optical axis B. The inclination of the deflecting surface 4a with respect to the optical axis B is, for example, 10.5°. The refracting surface 4b is a convex spherical or aspherical surface that is symmetrical with respect to the predetermined optical axis B and has a positive power with respect to the light incident from the deflecting surface 4a side along the optical axis B.

Figure 3A:
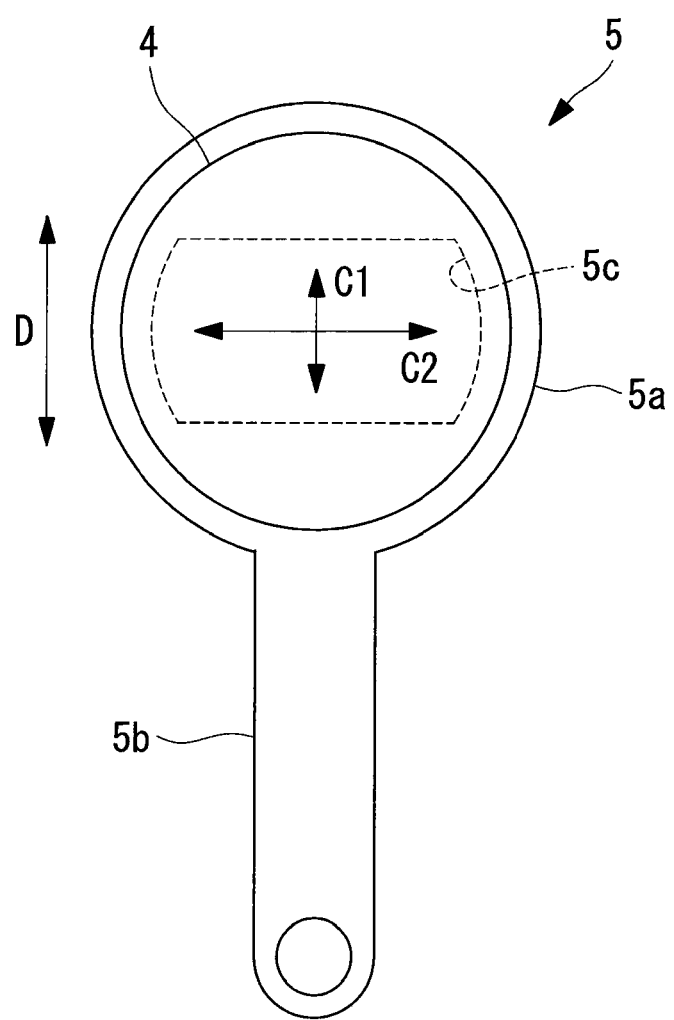
FIG. 3A is a front view of the optical component and a stop shown in FIG. 2, as viewed from the object side.
Figure 3B:
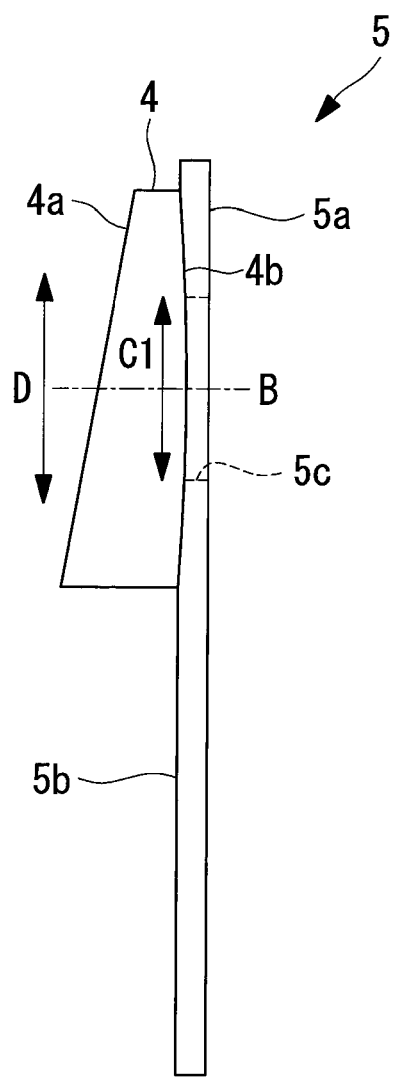
FIG. 3B is a side view of the optical component and stop in FIG. 3A.
Figure 4:
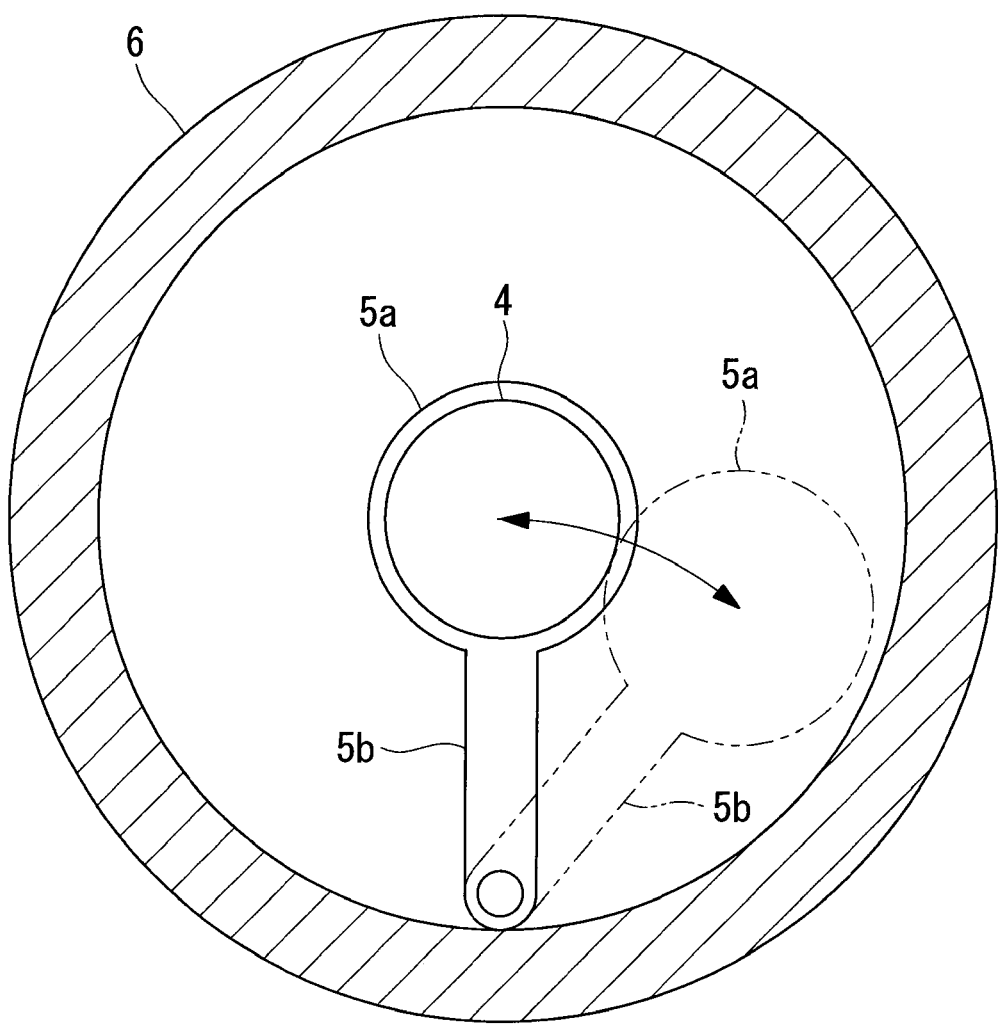
FIG. 4 shows the configuration and movement of a moving mechanism.

As shown in FIGS. 3A, 3B, and 4, the moving mechanism 5 includes a ring-like frame 5a, which supports the circumferential portion of the prism 4, an arm 5b having one end connected to the frame 5a, and a motor (not shown) that causes the arm 5b to pivot about the other end. Reference sign 6 denotes a lens frame that accommodates the objective optical system 2 therein. The moving mechanism 5 can move the prism 4 between an inserted position (first position), illustrated with a solid line, and a retracted position (second position), illustrated with a two-dot chain line, by pivoting the arm 5b. The inserted position is the position where the predetermined optical axis B of the prism 4 and the optical axis A of the objective optical system 2 are aligned. At the inserted position, the prism 4 is disposed such that the deflecting surface 4a faces the incident side. The retracted position is a position where the entire prism 4 is located on the radially outer side of the lenses constituting the objective optical system 2 and where the prism 4 does not interfere with the light passing through the objective optical system 2.

The moving mechanism 5 inserts and removes the prism 4 into and from the optical axis A in the vicinity of the aperture stop S, where the beam height is small. Thus, the diameters of the prism 4 and moving mechanism 5 may be small, enabling a reduction in the diameter of the overall image-acquisition device 1. Note that the position where the prism 4 is inserted is not limited to the vicinity of the aperture stop S, but may be appropriately changed.

As shown in FIGS. 3A and 3B, the frame 5a is fixed to the refracting surface 4b of the prism 4 and constitutes the stop having an opening 5c provided at a portion corresponding to the central portion of the prism 4. With this configuration, the stop moves between the retracted position and the inserted position, integrally with the prism 4. The opening 5c has an oblong shape having a short axis and a long axis, and a direction, C1, of the short axis matches an inclination direction, D, in which the deflecting surface 4a is inclined with respect to the optical axis B. An arrow C2 indicates the direction of the long axis.

Figure 5:
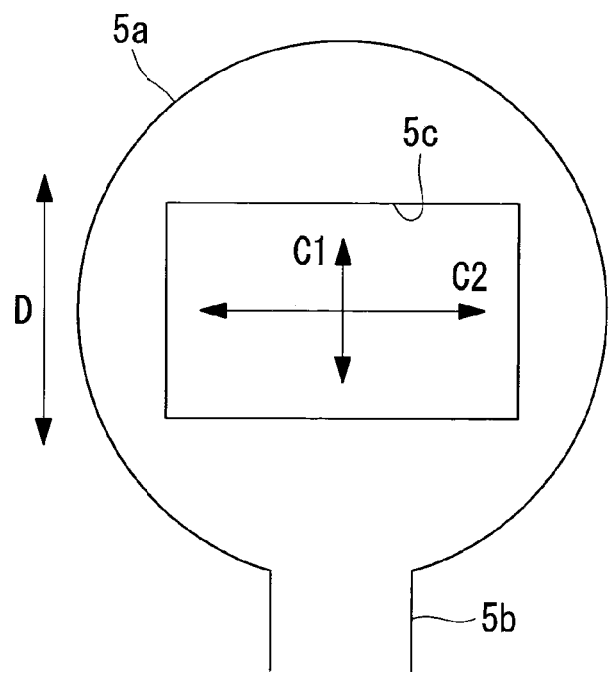
FIG. 5 shows a modification of an opening in the stop in FIG. 3A.
Figure 6:
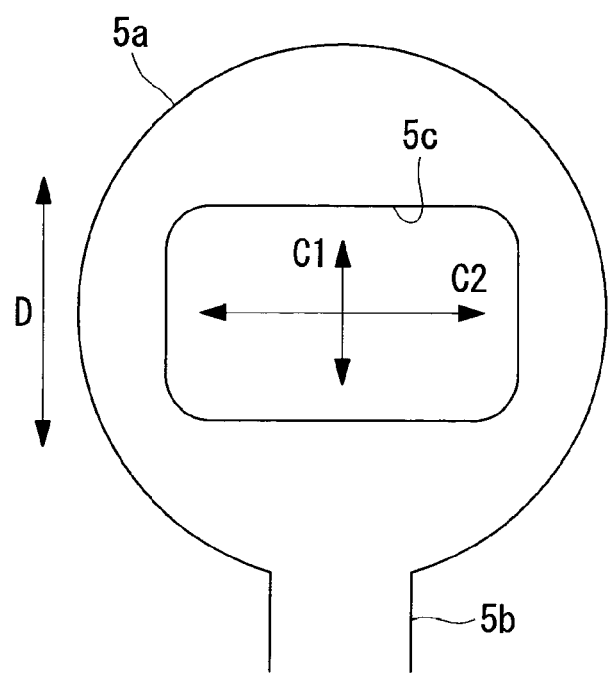
FIG. 6 shows another modification of the opening in the stop in FIG. 3A.
Figure 7:
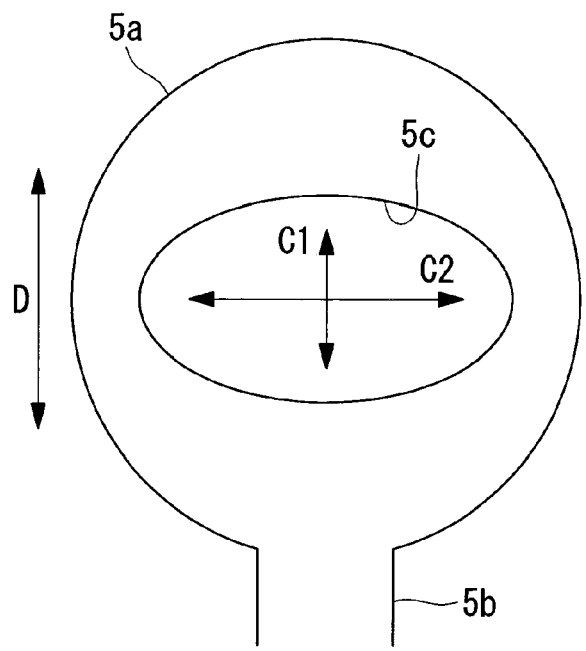
FIG. 7 shows another modification of the opening in the stop in FIG. 3A.

FIGS. 5 to 8 show modifications of the shape of the opening 5c. As shown in FIGS. 5 to 7, the opening 5c may have a rectangular shape, an elliptical shape, or a rectangular shape having rounded corners.

Figure 8:
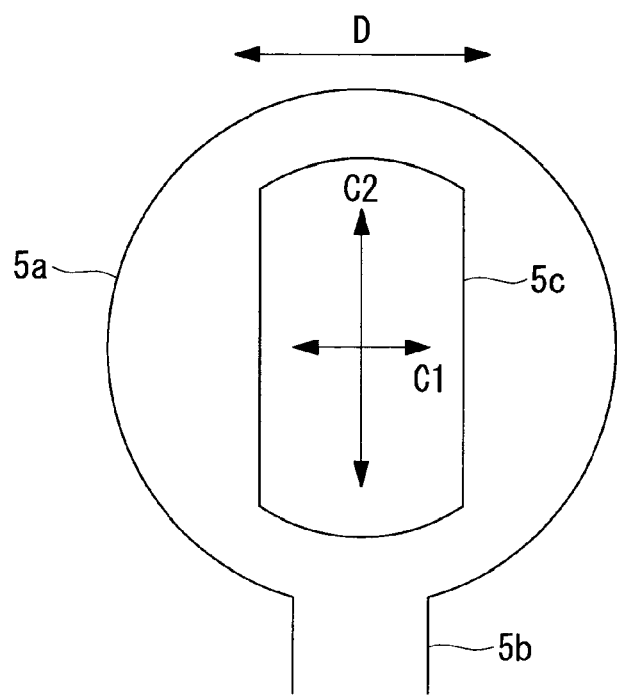
FIG. 8 shows another modification of the opening in the stop in FIG. 3A.

Furthermore, the direction C1 of the short axis of the opening 5c provided in the frame 5a is appropriately changed according to the relative orientations of the frame 5a and the deflecting surface 4a when disposed at the inserted position. For example, in FIG. 1, when the inclination direction D equals the depth direction (i.e., the direction perpendicular to the plane of the drawing), the opening 5c needs to be rotated by 90°, as shown in FIG. 8, from that shown in FIG. 3A.

Next, the operation of the thus-configured image-acquisition device 1 will be described.

With the image-acquisition device 1 according to this embodiment, by changing the position of the prism 4 between the retracted position and the inserted position with the moving mechanism 5, the observation direction can be switched between direct view and oblique view.

More specifically, in the direct-view observation state, in which the prism 4 is positioned at the retracted position, the optical axis A of the objective optical system 2 extends straight along the central axis of the objective optical system 2, and the light from an object positioned directly in front of the objective optical system 2 is incident on the objective optical system 2. Hence, it is possible to acquire a direct-view image showing a field of view positioned directly in front of the objective optical system 2. On the other hand, in the oblique-view observation state, in which the prism 4 is positioned at the inserted position, the incident-side optical axis A of the objective optical system 2 is deflected by the deflecting surface 4a, and the light from an object positioned obliquely in front of the objective optical system 2 is incident on the objective optical system 2. Hence, it is possible to acquire an oblique-view image showing a field of view positioned obliquely in front of the objective optical system 2.

Herein, in the oblique-view observation state, although the prism 4 having a larger refractive index than air decreases the air-equivalent length on the optical axis A of the objective optical system 2, thus moving the focus point in the direction away from the objective optical system 2, the positive power of the refracting surface 4b moves the focus point in the direction toward the objective optical system 2. In other words, in this embodiment, displacement of the focus point caused by the insertion of the prism 4 is corrected by the positive power of the refracting surface 4b, thus preventing the focus point from moving away when switched from the direct-view observation state to the oblique-view observation state. This is advantageous when, for example, observing a treatment tool projecting from the distal end of an endoscope to which the image-acquisition device 1 is applied, and it is possible to acquire an oblique-view image that is focused on the treatment tool positioned at a proximal side of the distal end of the endoscope.

Moreover, because the deflecting surface 4a is inclined with respect to the optical axis A, in the inclination direction D of the prism 4 (the direction in which the optical axis A is deflected), the shape of the prism 4 is asymmetrical with respect to the optical axis A. As a result, coma and astigmatism, which are asymmetrical aberrations, occur in the light passing through the prism 4 and the opening 5c. Typically, the amount of coma generated is proportional to the square of the size of the opening 5c, and the amount of astigmatism generated is proportional to the size of the opening 5c. Hence, by reducing the size of the opening 5c in the inclination direction D, in which the asymmetrical aberrations occur, the amount of asymmetrical aberrations generated can be reduced, whereby it is possible to acquire a high-quality oblique-view image.

Although the refracting surface 4b of the prism 4 has a positive power in this embodiment, instead, the refracting surface 4b may be a concave spherical or aspherical surface having a negative power.

With this configuration, when switching from the direct-view observation state to the oblique-view observation state, the focus point moves farther away. Thus, in applications where an object located at a distant place is observed with the oblique-view observation, this configuration enables acquisition of an oblique-view image in which a sharp image of the observation target is acquired.

Although the frame 5a also serves as the stop, and the stop is formed integrally with the prism 4 in this embodiment, instead, the stop may be a separate component from the frame 5a and the prism 4. In such a case, another moving mechanism may be provided so that the stop moves in accordance with the movement of the prism 4.

Figure 9:
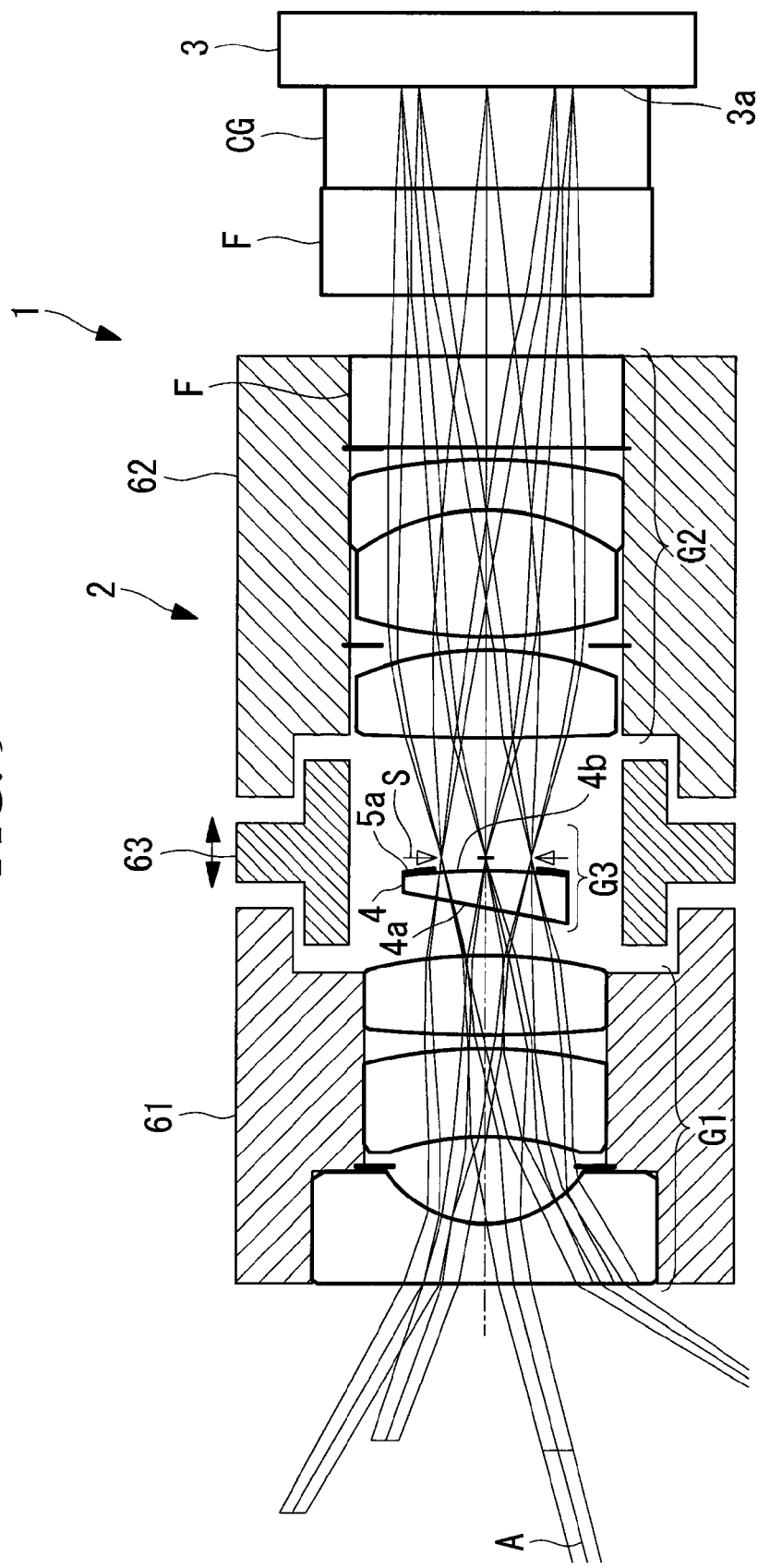
FIG. 9 shows the overall configuration of a modification of the image-acquisition device in FIG. 2.

In this embodiment, as shown in FIG. 9, it may be configured such that the position of a third group G3, which includes the prism 4, the moving mechanism 5, and the aperture stop S, is adjustable in the direction of the optical axis A, relative to the first group G1 and the second group G2. More specifically, the first group G1, the second group G2, and the third group G3 are held in separate lens frames 61, 62, and 63. The ends of the lens frame 63, which holds the third group G3, are fitted into the ends of the lens frames 61 and 62, which hold the first group G1 and the second group G2 in a nested manner, and the lens frame 63 is capable of moving in the direction of the optical axis A relative to the lens frames 61 and 62. With this configuration, the position of the third group G3 relative to the first group G1 and the second group G2 can be adjusted by the movement of the lens frame 63, and the focus point can be adjusted in the direction of the optical axis A.

As described above, although the displacement of the focus point due to the insertion of the prism 4 is corrected by the positive power of the refracting surface 4b, depending on manufacturing errors in the surface shape of the prism 4, it may not be possible to obtain sufficient focusing accuracy. Hence, by making final focus adjustments in the oblique-view observation state through fine adjustment of the position of the prism 4 in the direction of the optical axis A and then fixing the lens frame 63 to the lens frames 61 and 62, high focusing accuracy, which is difficult to achieve only by improving the dimensional tolerance of the prism 4, can be easily and reliably obtained.

Figure 10:
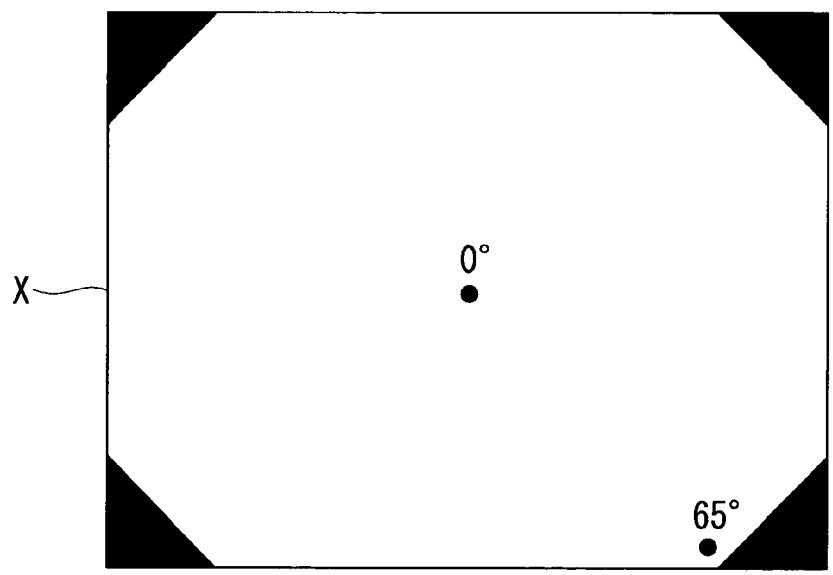
FIG. 10 is an example direct-view image acquired by the image-acquisition device in the direct-view observation state in FIG. 1.
Figure 11:
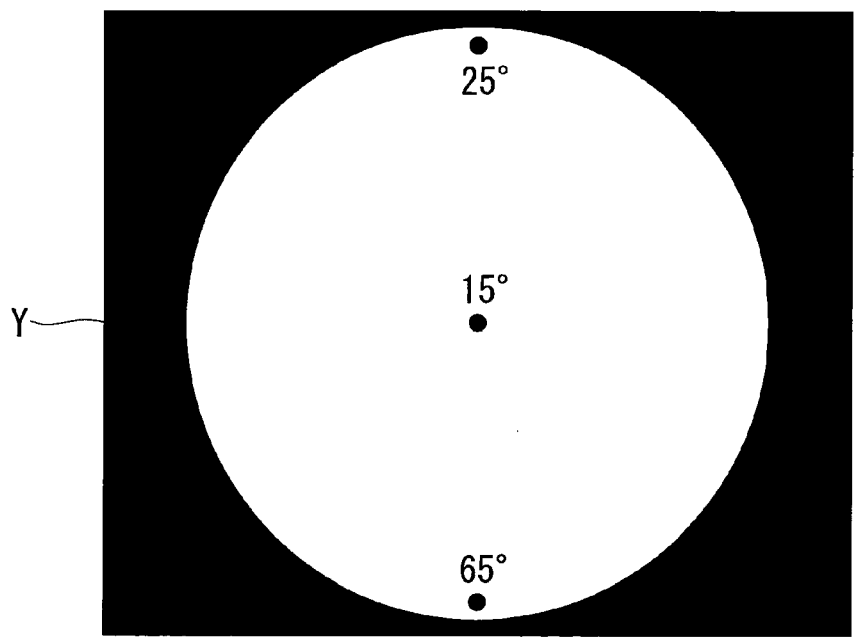
FIG. 11 is an example oblique-view image acquired by the image-acquisition device in the oblique-view observation state in FIG. 2.

In this embodiment, mask processing, in which a field-of-view mask having an opening is superposed, may be performed on a direct-view image or an oblique-view image, and the image subjected to the mask processing may be displayed on the display. In such a case, it is desirable that the image-acquisition device 1 use a typical field-of-view mask having an octagonal opening, as shown in FIG. 10, for a direct-view image X and use a field-of-view mask having a circular opening with a smaller diameter than the octagonal opening, as shown in FIG. 11, for an oblique-view image Y. In FIGS. 10 and 11, the black portions are the field-of-view masks, and the white portions are openings.

As shown in FIG. 2, in the oblique-view observation state, the angle of view of a portion of the field of view located on the radially outer side of the optical axis A is near 90°. The light coming from the area like this, having a large angle of view, toward the objective optical system 2 is vignetted by the members, such as a lens frame 6, around the objective optical system 2 and is not incident on the objective optical system 2. As a result, an oblique-view image Y in which the peripheral portion of the image is partially lost is acquired by the image-acquisition element 3.

In the example shown in FIG. 11, the objective optical system 2 having a half angle of view of about 65° is used, and the observation direction is tilted downward by 15° with respect to the direct-view direction. In this case, although a semicircular image, similar to that obtained with the direct-view observation, is obtained in the upper half of the field of view, the angle of view in the lower half of the field of view, at the lower right portion and the lower left portion, is 80° (in actuality, the angle of view is about 90°, due to the influence of distortion). Thus, the lower right portion and the lower left portion of the oblique-view image Y are lost. As a result, the upper part and the lower part of the field of view become asymmetrical as a whole.

To counter this problem, by concealing the portions where the image is lost with a field-of-view mask having a small circular opening, an oblique-view image Y that does cause a sense of incongruity to the observer can be displayed.

In this embodiment, the prism 4 may be provided at the inserted position so as to be rotatable about the optical axis A.

Rotation of the prism 4 about the optical axis A changes the direction of the incident-side optical axis A deflected by the deflecting surface 4a and changes the observation direction. Thus, the observable area can be increased. For example, in FIG. 2, although the field of view located obliquely on the lower side in the plane of the drawing is observed, when the prism 4 is rotated by 90°, the fields of view located obliquely on the left side and right side can be observed, and when the prism 4 is rotated by 180°, the field of view located obliquely on the upper side can be observed. Furthermore, by continuously rotating the prism 4, the peripheral portion around the field of view observed with the direct-view observation can be viewed.

Figure 12:
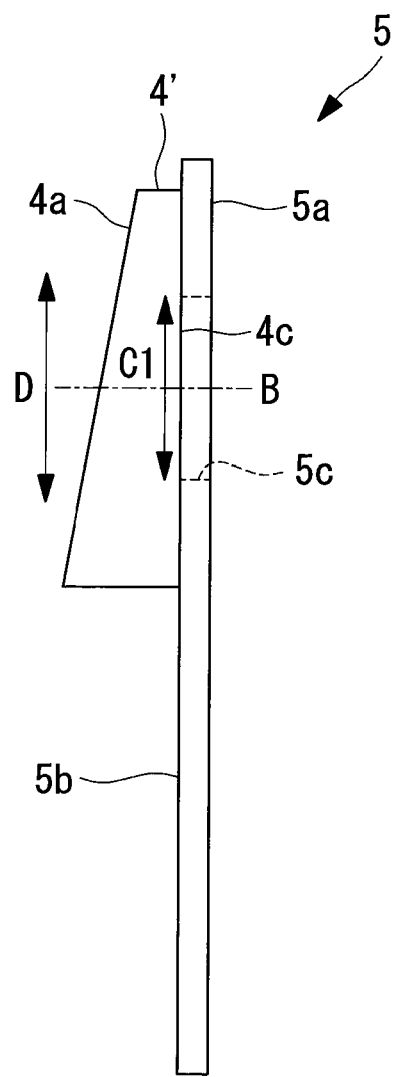
FIG. 12 is a side view showing a modification of the prism provided in the image-acquisition device shown in FIGS. 1 and 2.

Although the prism 4 having power has been described in this embodiment, a prism 4' that does not have power may be employed, as shown in FIG. 12. That is, the prism 4' may have a flat surface 4c intersecting the axis B at right angles, instead of the refracting surface 4b.

Although the displacement of the focus point due to the insertion of the prism 4 in the optical axis A cannot be corrected in this case, it is possible to effectively suppress astigmatism caused by the deflecting surface 4a, enabling acquisition of a high-quality oblique-view image.

From the above-described embodiment and modifications thereof, the following aspect of the invention is derived.

An aspect of the present invention is an image-acquisition device including an objective optical system that forms an optical image of an object; an image-acquisition element that captures an image of the optical image formed by the objective optical system; an optical component that is inserted into and removed from an optical axis of the objective optical system, at an intermediate position on the optical axis; and a moving mechanism that moves the optical component between a first position on the optical axis of the objective optical system and a second position off the optical axis. The optical component has a deflecting surface for deflecting the optical axis of the objective optical system and a refracting surface having power.

According to this aspect, when the optical component is disposed at the second position off the optical axis of the objective optical system, the optical axis of the objective optical system is straight, and a field of view located directly in front of the objective optical system is observed. On the other hand, when the optical component is disposed at the first position on the optical axis of the objective optical system, the optical axis of the light incident on the objective optical system is deflected by the deflecting surface, and a field of view positioned obliquely in front of the objective optical system is observed. Therefore, by moving the optical component between the first position and the second position with the moving mechanism, the observation direction can be switched between the direct-view observation and the oblique-view observation.

In this case, the displacement of the focus point caused by the insertion of the optical component into the optical axis is corrected by the power of the refracting surface. Thus, even in the oblique-view observation, an image that is focused at an appropriate position can be acquired by the image-acquisition element.

In the above-described aspect, the refracting surface may have a positive power.

With this configuration, the displacement of the focus point toward the object side, caused by the insertion of the optical component into the optical axis, is compensated for by the positive power of the refracting surface. Thus, in the oblique-view observation, an image that is focused at a position in front of the objective optical system can be acquired.

In the above-described aspect, the optical component may have two surfaces located along the optical axis with facing each other, one of the two surfaces being the deflecting surface, and the other being the refracting surface.

This configuration simplifies the shape of the optical component.

In the above-described aspect, the optical component may have a substantially wedge shape having the deflecting surface, which is a flat surface inclined with respect to the optical axis of the objective optical system, and the refracting surface, which is a spherical or aspherical surface that is symmetrical with respect to the optical axis of the objective optical system.

This configuration simplifies the shape of the optical component.

In the above-described aspect, the image-acquisition device may further include a stop provided in a vicinity of the optical component. The stop may have an oblong opening having a short axis and a long axis, and may be arranged such that the short axis of the opening is aligned with a direction in which the deflecting surface deflects the optical axis of the objective optical system, and the moving mechanism may move the optical component and the stop in an integrated manner.

With this configuration, aberrations are caused by the optical component inserted into the optical axis of the objective optical system, and, in particular, asymmetrical aberrations are caused in the direction in which the deflecting surface deflects the optical axis. Thus, by reducing the size of the opening of the stop in the deflection direction, the occurrence of the asymmetrical aberrations can be effectively suppressed.

REFERENCE SIGNS LIST 1 image-acquisition device
2 objective optical system
3 image-acquisition element
3a image-acquisition surface
4 prism (optical component)
4a deflecting surface
4b refracting surface
4c flat surface
5 moving mechanism
5a frame (stop)
6, 61, 62, and 63 lens frame
A optical axis
X direct-view image
Y oblique-view image

The invention claimed is:

1. An image-acquisition device consisting of:
   a single objective optical system;
   an image-acquisition element that captures an image of an optical image of an object formed by the objective optical system;
   an optical component that is inserted into and removed from an optical axis of the objective optical system, at an intermediate position on the optical axis; and
   a moving mechanism that moves the optical component between a first position on the optical axis of the objective optical system and a second position off the optical axis,
   wherein the optical component has a deflecting surface for deflecting the optical axis of the objective optical system and a refracting surface having power.

2. The image-acquisition device according to claim 1, wherein the refracting surface has a positive power.

3. the image-acquisition device according to claim 1, wherein
   the optical component has two surfaces located along the optical axis with facing each other, one of the two surfaces being the deflecting surface, and the other being the refracting surface.

4. The image-acquisition device according to claim 1, wherein the optical component has a substantially wedge shape having the deflecting surface, which is a flat surface inclined with respect to the optical axis of the objective optical system, and the refracting surface, which is a spherical or aspherical surface that is symmetrical with respect to the optical axis of the objective optical system.

5. The image-acquisition device according to claim 1, further comprising a stop provided in a vicinity of the optical component, wherein
   the stop has an oblong opening having a short axis and a long axis, and is arranged such that the short axis of the opening is aligned with a direction in which the deflecting surface deflects the optical axis of the objective optical system, and
   the moving mechanism moves the optical component and the stop in an integrated manner.

* * * * *